United States Patent [19]

Honeycutt

[11] Patent Number: 5,578,318
[45] Date of Patent: Nov. 26, 1996

[54] CONSUMABLE PRODUCT CONTAINING ABSORBENT COMPOSITION

[75] Inventor: Travis W. Honeycutt, Gainesville, Ga.

[73] Assignee: Isolyser Co., Inc., Norcross, Ga.

[21] Appl. No.: 447,658

[22] Filed: May 23, 1995

Related U.S. Application Data

[62] Division of Ser. No. 72,724, Jun. 7, 1993, Pat. No. 5,417,977, which is a division of Ser. No. 875,237, Apr. 28, 1992, Pat. No. 5,252,340, which is a continuation-in-part of Ser. No. 669,363, Mar. 14, 1991, abandoned, which is a continuation-in-part of Ser. No. 450,579, Dec. 14, 1989, abandoned.

[51] Int. Cl.$^6$ .............. A61K 9/70; A61K 9/14; A01N 25/34; A61F 13/15
[52] U.S. Cl. .............. 424/443; 424/402; 424/404; 424/405; 424/408; 424/411; 424/413; 424/489; 424/499; 424/501; 604/360; 604/904
[58] Field of Search .................. 424/402, 404, 424/405, 408, 411, 413, 443, 489, 499, 501; 604/360, 904

[56] References Cited

U.S. PATENT DOCUMENTS

| | | | |
|---|---|---|---|
| 3,578,619 | 5/1971 | Reeder | 536/114 |
| 3,637,657 | 1/1972 | Morii | 536/59 |
| 4,043,952 | 8/1977 | Ganslaw et al. | 536/114 |
| 4,952,550 | 8/1990 | Wallach | 604/368 |
| 4,959,341 | 9/1990 | Wallach et al. | 604/368 |
| 4,959,464 | 9/1990 | Yeh | 536/114 |

*Primary Examiner*—Carlos Azpuru
*Attorney, Agent, or Firm*—Malcolm B. Wittenberg

[57] ABSTRACT

A method of producing an absorbent composition. A polymeric material characterized as having surface anionic reactive sites is mixed with a source of multi-valent metal ions to render the polymeric material sorbent of aqueous liquids. A dispersant is then added to form a wet slurry which is subsequently dried to a granular consistency.

2 Claims, No Drawings

CONSUMABLE PRODUCT CONTAINING ABSORBENT COMPOSITION

This is a divisional of application Ser. No. 08/072,724, filed Jun. 7, 1993, now U.S. Pat. No. 5,417,977, which is a divisional of application Ser. No. 875,237 filed Apr. 28, 1992, now U.S. Pat. No. 5,252,340, which is a continuation-in-part of application Ser. No. 669,363 filed Mar. 14, 1991, now abandoned, which is in turn a continuation-in-part of application Ser. No. 450,579 filed Dec. 14, 1989, now abandoned.

TECHNICAL FIELD OF THE INVENTION

The present invention deals with a method of producing an absorbent composition. The composition is capable of absorbing and immobilizing aqueous bodily fluids and is designed for use in such diverse areas as diapers, feminine hygiene products, incontinent pads, surgical dressings and towels and in suction canisters, emesis basins and with arthroscopies and cystoscopies. Although such products have been made available in the past, prior to the present invention, there has not been a successful disposable product which is biodegradable and which is capable of absorbing such bodily fluids in an amount up to approximately 100 times the composition's own weight without significant mechanical intervention.

BACKGROUND OF THE INVENTION

As the general population becomes increasingly environmentally conscious, there has been a growing trend away from the use of disposable diapers and similar products. Present-day disposable diapers biodegrade at such a slow rate that, for all practical purposes, the products are considered non-biodegradable and, as such, can result in acute environmental damage. Large urban areas are simply running out of disposal areas and for those products which are non-recyclable, and which do not biodegrade, landfill sites can be considered toxically unsafe after the landfill capacity has been exhausted.

As a result of these concerns, many government agencies, both on the local and state levels, have gone so far as to completely outlaw the sale of disposable diapers and similar products. Although such products are convenient to use, particularly when a home laundry facility is unavailable, such as during vacation travel, unless a biodegradable product is at hand, disposable diapers and similar articles will simply disappear from grocery store shelves.

In addition to the need for biodegradable products, it is quite often desirable to provide a system for absorbing and preferably also disinfecting and/or immobilizing bodily fluids as these fluids can be infected with pathogenic bacteria, viruses, fungi and other matter. The potential source of pathogenicity has been acute with the knowledge and identification of certain pathogens such as hepatitis B and the AIDS virus.

It is further critical that an effective composition be provided that is capable of the immobilization and preferably solidification of infectious liquids without the need for any mechanical intervention. Preferably, the immobilized or solidified liquids can be made the subject of disinfection and appropriately landfilled, autoclaved or incinerated in accordance with local, State and Federal regulations. The need for such a protocol has been highlighted by the amendment made to 29 C.F.R. §1910.1030 which provides for the federal regulation under the Occupational Safety and Health Act, 29 U.S.C. 655, 657 to control bloodborne pathogens. Specifically, the Act calls for the establishment of an exposure control plan, the containment of specimens of blood or other potentially infectious materials and the general tightening of precautionary measures to minimize the spread of disease. Immobilization of blood, urine and other bodily fluids would greatly facilitate compliance with the above-referenced Act.

Congress has recently reported on the Medical Waste Tracking Act confirming that medical waste, although not a particular environmental problem, at least any more so than any other disposable trash or garbage, does represent a significant workplace hazard. As such, it is further contemplated that the present invention will enhance workplace safety.

It is thus an object of the present invention to provide a system for absorbing and/or immobilizing an entire host of diverse bodily fluids and other infectious or noninfectious aqueous liquids.

It is yet another object of the present invention to provide various disposable products containing the present absorbing and/or immobilizing agents which are biodegradable and thus environmentally preferred when compared to corresponding products currently available.

It is still a further object of the present invention to provide a superior means for containing and disinfecting potential infectious liquids and to allow for their disposal without the spread of pathogens and consequent disease.

It remains yet an additional object of the present invention to provide a method of producing an absorbent composition which is capable of absorbing up to 100 times by weight of a liquid without significant mechanical intervention or stirring.

These and further objects of the present invention will be more fully appreciated when considering the following disclosure and appended claims.

SUMMARY OF THE INVENTION

Broadly, the present invention is directed to a method of producing an absorbent composition a well as the composition produced by said method and various products embodying or containing said composition.

The method comprises producing a granular absorbent composition by heterogeneously surface reacting polymeric material with a source of multi-valent metal ions to render the polymeric material sorbent to aqueous liquids. The polymeric material is characterized as having surface anionic reactive sites. When dealing with water soluble polymeric material, liquid dispersant is added only after the dry admixture has been created to form a wet slurry which is subsequently dried to granular consistency. Preferably the composition is dispersed by the liquid dispersant but not dissolved therein.

It is hypothesized that the polymeric materials, when combined with multi-valent metal ions form ionic bridges between polymer chains on their grain surfaces which when mixed with aqueous based materials can create intimate mixtures without clumping or swelling.

The absorbing composition of the present invention is preferably in the form of a granular powder of a flour to rice consistency which can contain a sanitizing or disinfecting agent such as orthophenylphenol, T-amylphenol, ortho-benzylchlorophenol, citric acid, boric acid, triethanolamine, sodium borate or methylparaben. A wetting agent can be employed, for example, fluorinated polymers such as the Fluorads™ which are sold by Minnesota Mining & Manufacturing Co., or as Silwet™ surfactants which are available from Union Carbide or similar products of Dow Corning such as Dow 190, which are a class of ethoxylated silicone backbone polymers.

DETAILED DESCRIPTION OF THE INVENTION

It was originally hypothesized that a highly absorptive system could be composed of cross-linked polyacrylate salts. Although sodium and potassium polyacrylate salts work well under some conditions, such salts do not work well in the presence of electrolytes or at a low pH. At low pH, the polymer chains coil up and do not accept water, whereas at high electrolyte concentrations, the electronegatively charged chains are blanked by cations, thereby reducing their capacity to absorb water. Further, cross-linked polyacrylates are not biodegradable and their capacity to absorb is decreased by the presence of alcohols such as ethanol and isopropanol which are often found in medical settings. However, when suitable polymeric materials such as polyacryiamide and polyacrylic acids and their copolymers are "bridged" with a suitable multi-valent ion such as $Al^{+3}$ creating hydrophobic coated particles, their swelling capacity and rates are enhanced as they and their sensitivity to pH and solvents such as alcohols are decreased.

Others have even used glucosidic materials in producing absorbent compositions. For example, U.S. Pat. No. 4,959,341 teaches a composition comprising a carboxylic acid with a substantial hydrophobic region, a branched complex carbohydrate and cross-linking agent such that the composition can be hydrated and cross-linked simultaneously in the presence of a hydrating solution. Similarly, U.S. Pat. No. 4,952,550 teaches a method of making a particulate absorbent composition by reacting a carboxylated cellulosic material with cross-linking and hydrophobicity agents. The reaction product is separated and water removed therefrom until the composition is dehydrated and a particulate is formed of the absorbent material. However, these materials require significant mechanical intervention to achieve a homogeneous gel and they exhibit low sorbancies in the 10–20 part liquid to 1 part anhydrous prepared sorbent range. Furthermore, preparation of these materials in an anhydrous environment is quite inconvenient.

By contrast, the absorbent composition of the present invention employs polymeric material characterized as having surface anionic reactive sites such as carboxymethyl groups ($R_pCOO$) wherein $R_p$ comprises one or more members selected from the group consisting of glucosidics, acrylics, acrylic acid copolymers, polyacrylamide/acrylic acid copolymers, starch, carboxymethyl cellulose, carboxymethyl cellulose gum and sulphonated cellulose which are combined with multi-valent metal ions such as an $Al^{+3}$, $CA^{+2}$ and $Mg^{+2}$ to create hydrophobic coated particles. The combining should be carried out as a dry admixture when the polymer is water soluble. It is preferred that the ion $Al^{+3}$ be employed which can be derived from, for example, aluminum acetate or aluminum sulphate. This dry admixture can then be added to a liquid dispersant to form a wet slurry which is dried to a coarse granular consistency. The solvent is preferably an alcohol such as methanol, ethanol and isopropanol which, combined with or without a small amount of water, acts to hydrophobically coat the individual particles forming ionic bridges but does not act to dissolve the polymeric material. The combination of the dry and wet components creates a somewhat dry crumbly slurry that resembles slightly wetted sand.

The granular absorbent composition produced by the method recited above operates in the formation of ionic bridges formed between polymer chains and creation of hydrophobic coated particles by use of a multi-valent ion which is employed in combination with a liquid dispersant. The newly created particles, due to their hydrophobicity resist clumping and premature absorption in aqueous media resulting in particles which can absorb, for example, urine at a rate greater than 15 cc per second without any mechanical intervention which is the approximate human rate of urination and will absorb up to 100 parts by weight of liquid to one part solid. These absorption characteristics are repeatedly observed for liquids bearing both acid and alkaline pH's. In certain embodiments, this composition is polysaccharide based and it is thus biodegradable. Further, due to its biodegradable nature, such products as diapers containing this composition may be flushed into the sewer system as opposed to burial in landfills.

As optional expedients, the present composition can contain a polysiloxane derivative and super wetting agents, for example, Silwet™ 7614 which is available from Union Carbide and FC171, available from 3M which are flurochemical nonionic surfactants. Silwet™ 7614 is a combination of a siloxane and an ethoxylated end group residue. Also useful is Dow 190 which is a product sold by Dow Corning. Use of these wetting agents helps to disperse the particles as a slurry.

The absorbent composition of the present invention does not rely upon the use of a carboxylic acid in its formulation and, further, there is no need to add this composition to water to form a solution followed by precipitation with a multi-valent ion as is done in the prior art. The present composition can be added to water and/or saline which will then gel 20 to 100 times its weight virtually instantly without the need for mechanical intervention or stirring as a result primarily of the above-noted surface hydrophobicity of individual particles which tend to repel each other in aqueous media. By contrast, prior absorbers generally fail because they start absorbing too rapidly thereby gel blocking or hydrating to an excess forming undispersed clumps which precludes full swelling or absorption. These physical characteristics were clearly observed when dealing with the absorbing polymers disclosed in U.S. Pat. No. 4,090,013, even though the composition disclosed in this reference included sodium carboxymethyl cellulose which has been modified with various multi-valent ions including $Al^{+3}$. In this regard, it is noted that the prior art teaches reacting polymers and ions homogeneously while the present absorbing composition is created heterogeneously. The reactions which are carried out here are at the surface or boundary layer of the particles.

The preferred polymeric material can be, for example, polyacrylamide/acrylic acid copolymers, starch, carboxymethyl cellulose, carboxymethyl cellulose gum and sulphonated cellulose. The preferred carboxymethyl cellulose gum is sodium carboxymethyl cellulose. Multi-valent metal ions such as $Al^{+3}$ derived from, for example, aluminum acetate or aluminum sulfate act to form ionic bridges between these various ionic group polymer chains within each discrete particle. As noted above, the reactions are at the surfaces of each particle. This prevents the particles from absorbing each other and provides for the surprisingly good absorption characteristics observed. This particular gelling agent or absorbent works across a wide concentration of electrolytes and is capable of gelling blood and normal saline over a wide pH range.

One of the preferred immobilizing compositions comprises a cellulose derivative of the following structure which may or may not be partially cross-linked:

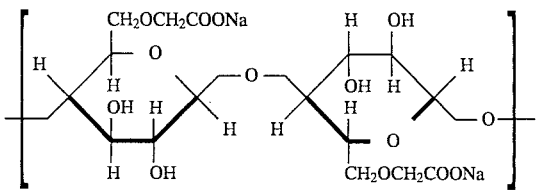

where the D.S. of the carboxyl groups are approximately 1 to 3.

The above is admixed with approximately 0.1–5% by weight of the following with the sodium salt being approximately 50–90% of the final mix but with 75–80% being preferred:

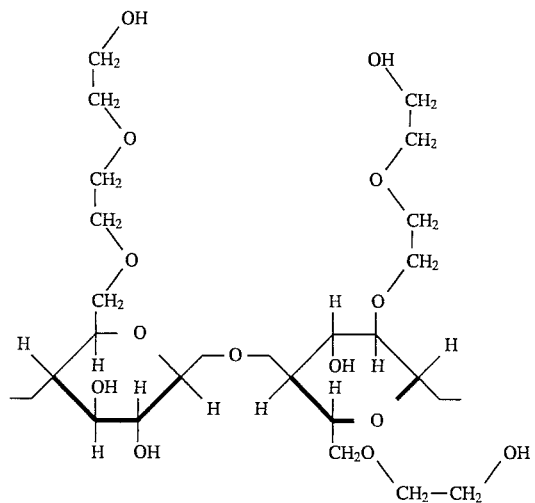

The "coarser" materials are preferred - materials similar to sand or coarse table salt work which wet more easily than materials with the consistency of fine sugar or flour.

Also included as possible preferred disinfectants in the system are phenols and their derivatives such as orthophenylphenol, benzylchlorophenol and amylphenol and their sodium salts at a level of 0.1–3.0% with 1.9–2.1% preferred.

As previously noted, when dealing with water soluble polymers, it is not only the ingredients but the manner which they have been combined which greatly facilitate the utility of the present invention. Firstly, the polymer and source of multi-valent ion are dry admixed. It is then contemplated that a fairly dry slurry be formed employing an alcohol such as ethanol, methanol or isopropanol or similar fluid in order to combine the anionic polymer with the anti-foaming agent and wetting agents. The anti-foaming agent, namely, polysiloxane, prevents clumping of the polymer granules while the wetting agent helps to hydrate the polymer. The source of trivalent metal ions such as aluminum acetate is poorly soluble in water. The polysiloxane derivatives initially form a hydrophobic barrier to keep the granular polymeric material separated but over a period one half to four minutes allow the individual grains to swell and grow thereby free-swelling through the volume of liquid to be solidified. In addition, these wetting agents act to prevent clumping and aid in the dispersion of the granular material before gel formation in the aqueous medium. In the event of salt bridging or ionic linking before dispersion, clumping would be visibly noticeable which is obviously an unacceptable quality or characteristic of such a composition. Only in practice of the present invention has polymeric material been capable of swelling, immobilizing and absorbing without significant mechanical intervention.

EXAMPLE I

A composition was prepared of the following ingredients.

| Ingredient | Amount | Percentage (By Weight) |
|---|---|---|
| Aqualon A-250 | 805.5 g. | 80.54 |
| Aluminum Acetate | 64.4 g. | 6.44 |
| Isopropyl Alcohol | 124.9 g. | 12.49 |
| FC-171 | 4.9 g. | 0.49 |
| Polysiloxane | 0.4 g. | 0.04 |

The composition was prepared by mixing the Aqualon A-250 in powdered form with aluminum acetate which is also in the form of a powder. This mixture was shaken for 15 minutes and the powdered ingredients mixed with the liquid ingredients. The liquids were premixed before addition to the powders. Isopropyl alcohol, FC-171 and the polysiloxane were combined in a separate bottle. The two bottles were prepared and agitated for five minutes and were then mixed. The combination was allowed to stand for four hours and then spread onto aluminum foil and allowed to dry overnight. The dried powder was then pulverized and sifted and put in a container the next day.

It was recognized that the A-250 does not "wet" well. However, this problem was overcome by the addition of the wetting agent FC-171. It, as well as the Silwet L-7614, a non-ionic ethylene oxide modified polysiloxane act to reduce surface tension to a range of approximately 20–30 dynes/cm$^2$. Alternatively, a small amount (5–25%) of the mixture can be $H_2O$. The prior addition of a small amount of $H_2O$ increases the free swell of the gelling material and increases the wetting rate. However, at the upper limit, clumping of the mix may occur requiring considerable sieving and pulverizing.

It was found that the product of Example I at the 1–3% solids level is capable of immediately wetting and gelling blood, saline and other bodily fluids without mechanical intervention.

Aqualon A-250, is a brand of high molecular weight sodium CMC sold by Hercules and is difficult to dissolve without considerable heat, time and stirring. Even then, as the examples below will illustrate, it does not form an immobilizing gel, but instead forms a highly viscous liquid.

EXAMPLE II

A composition was prepared by first combining the dry ingredients comprising 3200 g of Aqualon A-250 CMC gum with 512 g of aluminum acetate. These ingredients were added to a ball mill jar with 18 marbles and mixed for 15 minutes.

The wet ingredients were individually mixed by adding 800 g of isopropanol to 192 g of orthobenzylparachlorophenol (OBCP) sold under the trademark Dowicide by the Dow Chemical Company. To these liquid ingredients were further added 38.4 g of the wetting agent FC-171 and 3.2 g of Antifoam A, a polysiloxane solid by Dow Corning. These liquid ingredients were shaken for two to three minutes and added to the dry components in the mixing jar into which an additional 18 marbles were added. The pasty composition was mixed for 30 minutes until thoroughly mixed and spread on a horizontal surface as a thin sheet and dried overnight. The composition was then sieved and was suitable for use.

It was noted that when approximately one-quarter of the weight of the dry ingredients were employed as the liquid component, an appropriate wet powder was achieved, ideal for producing the desired product. Of the total ingredients, approximately 5–50% (by weight) of the alcohol component can be employed with 10–20% (by weight) being preferred. The wetting agent, such as FC 171, should be used between approximately 0.1–1.0% (by weight) while the polysiloxane derivative should be used between 0.1–0.5% (by weight).

In each of the examples, III–XXIV, the dry ingredients were weighed separately and mixed together in a plastic jar for two minutes. The wet ingredients were likewise weighed separately and mixed together in a plastic jar. After preparation of the liquid ingredients, they were added to the dry ingredients in a plastic jar and capped. Each of the mixes were shaken for two minutes and allowed to stand for four hours to swell. The mixes were then spread onto an aluminum foil sheet and dried at ambient temperatures for eight hours.

EXAMPLE III

|  | Manufacturer | Weight | % of Mix |
| --- | --- | --- | --- |
| Dry Ingredients |  |  |  |
| Aqualon A-250 | Aqualon | 805.5 | 80.55 |
| Aluminum Acetate | Niacet | 64.4 | 6.44 |
| Wet Ingredients |  |  |  |
| Isopropyl Alcohol | Ashland | 124.9 | 12.49 |
| FC 171 | 3M | 4.8 | 0.48 |
| Antifoam A | Dow | 0.4 | 0.04 |
| Total |  | 1000.0 | 100.00 |

EXAMPLE IV

|  | Manufacturer | Weight | % of Mix |
| --- | --- | --- | --- |
| Dry Ingredients |  |  |  |
| Aqualon A-250 | Aqualon | 805.5 | 80.51 |
| Aluminum Acetate | Niacet | 64.4 | 6.44 |
| Wet Ingredients |  |  |  |
| Isopropyl Alcohol | Ashland | 124.9 | 12.48 |
| FC 171 | 3M | 4.8 | 0.49 |
| Antifoam A | Dow | 0.8 | 0.09 |
| Total |  | 1000.4 | 100.00 |

EXAMPLE V

|  | Manufacturer | Weight | % of Mix |
| --- | --- | --- | --- |
| Dry Ingredients |  |  |  |
| Aqualon A-250 | Aqualon | 805.5 | 80.47 |
| Aluminum Acetate | Niacet | 64.4 | 6.43 |
| Wet Ingredients |  |  |  |
| Isopropyl Alcohol | Ashland | 124.9 | 12.47 |
| FC 171 | 3M | 4.8 | 0.48 |
| Antifoam A | Dow | 0.4 | 0.04 |

-continued

|  | Manufacturer | Weight | % of Mix |
| --- | --- | --- | --- |
| Fragrance 6678-AP | IFF | 1.0 | 0.1 |
| Total |  | 1001.4 | 99.99 |

EXAMPLE VI

|  | Manufacturer | Weight | % of Mix |
| --- | --- | --- | --- |
| Dry Ingredients |  |  |  |
| Aqualon A-250 | Aqualon | 805.5 | 80.30 |
| Aluminum Acetate | Niacet | 64.4 | 6.43 |
| Wet Ingredients |  |  |  |
| Isopropyl Alcohol | Ashland | 124.9 | 12.46 |
| FC 171 | 3M | 4.8 | 0.48 |
| Antifoam A | Dow | 0.4 | 0.04 |
| Fragrance 6678-AP | IFF | 2.0 | 0.2 |
| Total |  | 1002.0 | 100.00 |

EXAMPLE VII

|  | Manufacturer | Weight | % of Mix |
| --- | --- | --- | --- |
| Dry Ingredients |  |  |  |
| Aqualon A-250 | Aqualon | 805.5 | 63.24 |
| Aluminum Acetate | Niacet | 64.4 | 5.05 |
| Wet Ingredients |  |  |  |
| Isopropyl Alcohol | Ashland | 374.7 | 29.42 |
| FC 171 | 3M | 4.8 | 0.38 |
| Antifoam A | Dow | 1.2 | 0.09 |
| Silwet L-7614 | Union Carbide | 5.0 | 0.40 |
| Dowicide A | Dow Chemical | 18.0 | 1.41 |
| Total |  | 1273.6 | 99.99 |

EXAMPLE VIII

|  | Manufacturer | Weight | % of Mix |
| --- | --- | --- | --- |
| Dry Ingredients |  |  |  |
| Aqualon A-250 | Aqualon | 805.5 | 71.06 |
| Aluminum Acetate | Niacet | 64.4 | 5.68 |
| Wet Ingredients |  |  |  |
| Isopropyl Alcohol | Ashland | 249.0 | 21.97 |
| FC 171 | 3M | 4.8 | 0.42 |
| Antifoam A | Dow Corning | 4.8 | 0.42 |
| Silwet L-7614 | Union Carbide | 5.0 | 0.44 |
| Total |  | 1133.5 | 99.99 |

EXAMPLE IX

|  | Manufacturer | Weight | % of Mix |
| --- | --- | --- | --- |
| Dry Ingredients |  |  |  |
| Aqualon A-250 | Aqualon | 805.5 | 75.66 |
| Aluminum Acetate | Niacet | 64.4 | 6.05 |

|  | Manufacturer | Weight | % of Mix |
|---|---|---|---|
| Wet Ingredients | | | |
| A | | | |
| Isopropyl Alcohol | Ashland | 124.9 | 11.73 |
| FC 171 | 3M | 4.8 | 0.45 |
| Silwet L-7614 | Union Carbide | 5.0 | 0.47 |
| B | | | |
| Isopropyl Alcohol | Ashland | 50.0 | 4.70 |
| Tap H$_2$O | | 10.0 | 0.94 |
| Total | | 1064.4 | 100.0 |

EXAMPLE X

|  | Manufacturer | Weight | % of Mix |
|---|---|---|---|
| Dry Ingredients | | | |
| Aqualon A-250 | Aqualon | 805.5 | 74.96 |
| Aluminum Acetate | Niacet | 64.4 | 5.99 |
| Wet Ingredients | | | |
| A | | | |
| Isopropyl Alcohol | Ashland | 124.9 | 11.62 |
| FC 171 | 3M | 4.8 | 0.45 |
| Silwet L-7614 | Union Carbide | 5.0 | 0.46 |
| B | | | |
| Isopropyl Alcohol | Ashland | 50.0 | 4.65 |
| Tap H$_2$O | | 20.0 | 1.86 |
| Total | | 1074.4 | 99.99 |

EXAMPLE XI

|  | Manufacturer | Weight | % of Mix |
|---|---|---|---|
| Dry Ingredients | | | |
| Aqualon A-250 | Aqualon | 805.5 | 74.27 |
| Aluminum Acetate | Niacet | 64.4 | 5.94 |
| Wet Ingredients | | | |
| A | | | |
| Isopropyl Alcohol | Ashland | 124.9 | 11.51 |
| FC 171 | 3M | 4.8 | 0.44 |
| Silwet L-7614 | Union Carbide | 5.0 | 0.46 |
| B | | | |
| Isopropyl Alcohol | Ashland | 50.0 | 4.61 |
| Tap H$_2$O | | 30.0 | 2.77 |
| Total | | 1084.6 | 100.0 |

EXAMPLE XII

|  | Manufacturer | Weight | % of Mix |
|---|---|---|---|
| Dry Ingredients | | | |
| Aqualon A-250 | Aqualon | 805.5 | 73.59 |
| Aluminum Acetate | Niacet | 64.4 | 5.88 |

|  | Manufacturer | Weight | % of Mix |
|---|---|---|---|
| Wet Ingredients | | | |
| A | | | |
| Isopropyl Alcohol | Ashland | 124.9 | 11.41 |
| FC 171 | 3M | 4.8 | 0.44 |
| Silwet L-7614 | Union Carbide | 5.0 | 0.46 |
| B | | | |
| Isopropyl Alcohol | Ashland | 50.0 | 4.57 |
| Tap H$_2$O | | 40.0 | 3.65 |
| Total | | 1094.6 | 100.0 |

EXAMPLE XIII

|  | Manufacturer | Weight | % of Mix |
|---|---|---|---|
| Dry Ingredients | | | |
| Aqualon A-250 | Aqualon | 805.5 | 72.92 |
| Aluminum Acetate | Niacet | 64.4 | 5.83 |
| Wet Ingredients | | | |
| A | | | |
| Isopropyl Alcohol | Ashland | 124.9 | 11.31 |
| FC 171 | 3M | 4.8 | 0.43 |
| Silwet L-7614 | Union Carbide | 5.0 | 0.45 |
| B | | | |
| Isopropyl Alcohol | Ashland | 50.0 | 4.53 |
| Tap H$_2$O | | 50.0 | 4.53 |
| Total | | 1104.6 | 100.0 |

EXAMPLE XIV

|  | Manufacturer | Weight | % of Mix |
|---|---|---|---|
| Dry Ingredients | | | |
| Aqualon A-250 | Aqualon | 805.5 | 74.03 |
| Aluminum Acetate | Niacet | 64.4 | 5.92 |
| Wet Ingredients | | | |
| A | | | |
| OBCP | Dow | 23.4 | 2.15 |
| Isopropyl Alcohol | Aldrich | 124.9 | 11.48 |
| FC 171 | 3M | 4.8 | 0.44 |
| Silwet L-7614 | Union Carbide | 5.0 | 0.46 |
| B | | | |
| Isopropyl Alcohol | Aldrich | 50.0 | 4.60 |
| H$_2$O | | 10.0 | 0.92 |
| Total | | 1088.0 | 100.0 |

EXAMPLE XV

|  | Manufacturer | Weight | % of Mix |
|---|---|---|---|
| Dry Ingredients | | | |
| Aqualon A-250 | Aqualon | 805.5 | 773.36 |
| Aluminum Acetate | Niacet | 64.4 | 5.86 |
| Wet Ingredients | | | |
| A | | | |
| OBCP | Dow | 23.4 | 2.13 |

-continued

|  | Manufacturer | Weight | % of Mix |
|---|---|---|---|
| Isopropyl Alcohol | Aldrich | 124.9 | 11.38 |
| FC 171 | 3M | 4.8 | 0.44 |
| Silwet L-7614 | Union Carbide | 5.0 | 0.46 |
| B |  |  |  |
| Isopropyl Alcohol | Aldrich | 50.0 | 4.55 |
| H₂O |  | 20.0 | 1.82 |
| Total |  | 1098.0 | 100.0 |

EXAMPLE XVI

|  | Manufacturer | Weight | % of Mix |
|---|---|---|---|
| Dry Ingredients |  |  |  |
| Aqualon A-250 | Aqualon | 805.5 | 72.70 |
| Aluminum Acetate | Niacet | 64.4 | 5.81 |
| Wet Ingredients |  |  |  |
| A |  |  |  |
| OBCP | Dow | 23.4 | 2.11 |
| Isopropyl Alcohol | Aldrich | 124.9 | 11.27 |
| FC 171 | 3M | 4.8 | 0.43 |
| Silwet L-7614 | Union Carbide | 5.0 | 0.45 |
| B |  |  |  |
| Isopropyl Alcohol | Aldrich | 50.0 | 4.51 |
| H₂O |  | 30.0 | 2.71 |
| Total |  | 1108.0 | 99.99 |

EXAMPLE XVII

|  | Manufacturer | Weight | % of Mix |
|---|---|---|---|
| Dry Ingredients |  |  |  |
| Aqualon A-250 | Aqualon | 805.5 | 72.05 |
| Aluminum Acetate | Niacet | 64.4 | 5.76 |
| Wet Ingredients |  |  |  |
| A |  |  |  |
| OBCP | Dow | 23.4 | 2.09 |
| Isopropyl Alcohol | Aldrich | 124.9 | 11.17 |
| FC 171 | 3M | 4.8 | 0.43 |
| Silwet L-7614 | Union Carbide | 5.0 | 0.45 |
| B |  |  |  |
| Isopropyl Alcohol | Aldrich | 50.0 | 4.47 |
| H₂O |  | 40.0 | 3.58 |
| Total |  | 1118.0 | 100.0 |

EXAMPLE XVIII

|  | Manufacturer | Weight | % of Mix |
|---|---|---|---|
| Dry Ingredients |  |  |  |
| Aqualon A-250 | Aqualon | 805.5 | 71.41 |
| Aluminum Acetate | Niacet | 64.4 | 5.71 |
| Wet Ingredients |  |  |  |
| A |  |  |  |
| OBCP | Dow | 23.4 | 2.07 |

-continued

|  | Manufacturer | Weight | % of Mix |
|---|---|---|---|
| Isopropyl Alcohol | Aldrich | 124.9 | 11.07 |
| FC 171 | 3M | 4.8 | 0.43 |
| Silwet L-7614 | Union Carbide | 5.0 | 0.44 |
| B |  |  |  |
| Isopropyl Alcohol | Aldrich | 50.0 | 4.43 |
| H₂O |  | 40.0 | 4.43 |
| Total |  | 1128.0 | 99.99 |

EXAMPLE XIX

|  | Manufacturer | Weight | % of Mix |
|---|---|---|---|
| Dry Ingredients |  |  |  |
| Aqualon A-250 | Aqualon | 80.5 | 62.31 |
| Aluminum Acetate | Niacet | 4.8 | 3.71 |
| Wet Ingredients |  |  |  |
| A |  |  |  |
| Isopropyl Alcohol | Ashland | 12.5 | 9.67 |
| Silwet L-7614 | Union Carbide | 2.0 | 1.55 |
| OBCP | Dow | 2.3 | 1.78 |
| Antifoam A | Dow | 4.8 | 3.71 |
| B |  |  |  |
| Isopropyl Alcohol | Ashland | 10.0 | 7.74 |
| Tap H₂O |  | 10.0 | 7.74 |
| Total |  | 129.2 | 99.99 |

EXAMPLE XX

|  | Manufacturer | Weight | % of Mix |
|---|---|---|---|
| Dry Ingredients |  |  |  |
| Aqualon A-250 | Aqualon | 80.5 | 62.31 |
| Aluminum Acetate | Niacet | 4.8 | 3.71 |
| Sipernat HR-22 | Degussa | 2.3 | 1.78 |
| Wet Ingredients |  |  |  |
| A |  |  |  |
| Isopropyl Alcohol | Ashland | 12.5 | 9.67 |
| Silwet L-7614 | Union Carbide | 2.0 | 1.55 |
| One Stroke Vesphene se | Calgon Vestal | 6.4 | 4.95 |
| Antifoam A | Dow | 4.8 | 3.71 |
| B |  |  |  |
| Isopropyl Alcohol | Ashland | 10.0 | 7.74 |
| Tap H₂O |  | 5.9 | 4.67 |
| Total |  | 129.2 | 100.00 |

EXAMPLE XXI

|  | Manufacturer | Weight | % of Mix |
|---|---|---|---|
| Dry Ingredients |  |  |  |
| Aqualon A-250 | Aqualon | 80.5 | 64.71 |
| Aluminum Acetate | Niacet | 4.8 | 3.86 |
| Sipernat HR-22 | Degussa | 2.3 | 1.95 |

-continued

| | Manufacturer | Weight | % of Mix |
|---|---|---|---|
| Wet Ingredients | | | |
| A | | | |
| Isopropyl Alcohol | Ashland | 12.5 | 10.05 |
| Silwet L-7614 | Union Carbide | 2.0 | 1.60 |
| One Stroke Vesphene H | Calgon Vestal | 7.7 | 6.19 |
| Antifoam A | Dow | 2.3 | 1.85 |
| B | | | |
| Isopropyl Alcohol | Ashland | 10.0 | 8.04 |
| Tap H₂O | | 4.6 | 3.70 |
| Total | | 124.4 | 100.00 |

EXAMPLE XXII

| | Manufacturer | Weight | % of Mix |
|---|---|---|---|
| Dry Ingredients | | | |
| Aqualon A-250 | Aqualon | 80.5 | 62.31 |
| Aluminum Acetate | Niacet | 4.8 | 3.71 |
| Sipernat HR-22 | Degussa | 2.3 | 1.78 |
| Wet Ingredients | | | |
| A | | | |
| Isopropyl Alcohol | Ashland | 12.5 | 9.67 |
| Silwet L-7614 | Union Carbide | 1.0 | 0.77 |
| FC 171 | 3M | 1.0 | 0.77 |
| One Stroke Vesphene se | Calgon Vestal | 6.4 | 4.95 |
| Antifoam A | Dow | 4.8 | 3.71 |
| B | | | |
| Isopropyl Alcohol | Ashland | 10.0 | 7.74 |
| Tap H₂O | | 5.9 | 4.67 |
| Total | | 129.2 | 100.08 |

EXAMPLE XXIII

| | Manufacturer | Weight | % of Mix |
|---|---|---|---|
| Dry Ingredients | | | |
| Aqualon A-250 | Aqualon | 80.5 | 2.61 |
| Aluminum Acetate | Niacet | 6.4 | 0.21 |
| Wet Ingredients | | | |
| H₂O | | 3000.0 | 97.18 |
| Total | | 3086.9 | 100.00 |

EXAMPLE XXIV

| Dry Ingredients | Manufacturer | Weight | % of Mix |
|---|---|---|---|
| Aqualon A-250 | Aqualon | | 100.00 |

When, in the above-recited examples, the liquid ingredients were segregated as "A" and "B," they were added sequentially to the dry ingredients as "A" and then "B."

In each instance, the mix was tested for absorption in tap water and saline by weighing a 1.5 gram sample and adding it to 50 grams of liquid media in an uncovered plastic cup with no mixing or stirring. At the same time, the cup containing the absorbent and adsorbate was poured into a kitchen strainer and allowed to drain for two to four seconds into a weighing pan placed onto a scale that records in increments of 1/10 of a gram. The amount of unabsorbed liquid was recorded and subtracted from the starting amount which provided the absorbed amount. From these calculations, the percent of absorbance was recorded as follows:

EXAMPLE III

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 28.4 | 21.6 | 43.2 |
| 2 | 50 | 00.0 | 50.0 | 100.0 |
| Saline Absorbance | | | | |
| 1 | 50 | 34.0 | 16.0 | 32.0 |
| 2 | 50 | 17.7 | 32.3 | 64.6 |
| 4 | 50 | 10.4 | 39.6 | 79.2 |
| 8 | 50 | 7.5 | 42.5 | 85.0 |
| 16 | 50 | 7.7 | 42.3 | 84.6 |

EXAMPLE IV

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 0.8 | 49.2 | 98.4 |
| 2 | 50 | 0.0 | 50.0 | 100.0 |
| Saline Absorbance | | | | |
| 1 | 50 | 13.5 | 36.5 | 73.0 |
| 2 | 50 | 11.3 | 38.7 | 77.4 |
| 4 | 50 | 6.5 | 43.5 | 87.0 |
| 8 | 50 | 2.8 | 47.2 | 94.4 |
| 16 | 50 | 1.9 | 48.1 | 96.2 |

EXAMPLE V

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 19.2 | 30.8 | 61.2 |
| 2 | 50 | 1.9 | 48.1 | 96.6 |
| 4 | 50 | 0.0 | 50.0 | 100.0 |
| Saline Absorbance | | | | |
| 1 | 50 | 19.9 | 30.1 | 60.2 |
| 2 | 50 | 15.2 | 34.8 | 69.6 |
| 4 | 50 | 9.1 | 40.9 | 81.8 |

-continued

| Elapsed Time in Minutes | Starting Quantity of Liquid in Grams | Grams Retrieved Liquid | Grams Absorbed Liquid | Percent Absorbed Liquid |
|---|---|---|---|---|
| 8 | 50 | 4.9 | 45.1 | 90.2 |
| 16 | 50 | 8.2 | 41.8 | 83.6 |

EXAMPLE VI

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 23.4 | 26.6 | 53.2 |
| 2 | 50 | 18.0 | 32.0 | 64.0 |
| 4 | 50 | 8.3 | 41.7 | 83.4 |
| 8 | 50 | 1.2 | 48.8 | 97.6 |
| 16 | 50 | 0.0 | 50.0 | 100.0 |
| Saline Absorbance | | | | |
| 1 | 50 | 24.7 | 25.3 | 50.0 |
| 2 | 50 | 21.0 | 29.0 | 58.0 |
| 4 | 50 | 13.4 | 36.6 | 73.2 |
| 8 | 50 | 14.0 | 36.0 | 72.0 |
| 16 | 50 | 11.6 | 38.4 | 76.8 |

EXAMPLE VII

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 25.6 | 24.4 | 48.8 |
| 2 | 50 | 7.5 | 42.5 | 85.0 |
| 4 | 50 | 0.0 | 50.0 | 100.0 |
| Saline Absorbance | | | | |
| 1 | 50 | 30.5 | 19.5 | 39.0 |
| 2 | 50 | 23.2 | 26.8 | 53.6 |
| 4 | 50 | 11.7 | 38.3 | 76.6 |
| 8 | 50 | 9.5 | 40.5 | 85.0 |
| 16 | 50 | 11.3 | 38.7 | 77.4 |

EXAMPLE VIII

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 20.8 | 29.2 | 58.4 |
| 2 | 50 | 6.4 | 43.6 | 87.2 |
| 4 | 50 | 0.0 | 50.0 | 100.0 |
| Saline Absorbance | | | | |
| 1 | 50 | 19.0 | 31.0 | 62.0 |
| 2 | 50 | 15.1 | 34.9 | 69.8 |
| 4 | 50 | 5.7 | 44.3 | 88.6 |
| 8 | 50 | 7.8 | 42.2 | 88.4 |
| 16 | 50 | 1.2 | 48.8 | 97.6 |

EXAMPLE IX

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 6.4 | 43.6 | 87.2 |
| 2 | 50 | 1.3 | 48.7 | 97.4 |
| 4 | 50 | 0.0 | 50.0 | 100.0 |
| Saline Absorbance | | | | |
| 1 | 50 | 21.4 | 28.6 | 57.2 |
| 2 | 50 | 13.4 | 36.6 | 73.2 |
| 4 | 50 | 11.1 | 38.9 | 77.8 |
| 8 | 50 | 5.8 | 44.2 | 88.4 |
| 16 | 50 | 5.7 | 44.3 | 88.6 |
| 32 | 50 | 1.1 | 48.9 | 97.8 |

EXAMPLE X

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 9.7 | 40.3 | 80.6 |
| 2 | 50 | 0.8 | 49.2 | 98.4 |
| 4 | 50 | 0.0 | 50.0 | 100.0 |
| Saline Absorbance | | | | |
| 1 | 50 | 17.0 | 33.0 | 66.0 |
| 2 | 50 | 9.8 | 40.2 | 80.24 |
| 4 | 50 | 4.4 | 45.6 | 91.2 |
| 8 | 50 | 6.5 | 43.5 | 87.0 |
| 16 | 50 | 1.6 | 48.4 | 96.8 |
| 32 | 50 | 4.3 | 45.7 | 91.4 |

EXAMPLE XI

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 1.2 | 48.8 | 97.6 |
| 2 | 50 | 0.0 | 50.0 | 100.0 |
| Saline Absorbance | | | | |
| 1 | 50 | 14.5 | 35.5 | 71.0 |
| 2 | 50 | 6.9 | 43.1 | 86.2 |
| 4 | 50 | 5.8 | 44.2 | 88.4 |
| 8 | 50 | 1.3 | 48.7 | 97.4 |
| 16 | 50 | 1.7 | 48.3 | 96.6 |
| 32 | 50 | 2.4 | 47.6 | 95.2 |

EXAMPLE XII

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 0.0 | 50.0 | 100.0 |

-continued

| Elapsed Time in Minutes | Starting Quantity of Liquid in Grams | Grams Retrieved Liquid | Grams Absorbed Liquid | Percent Absorbed Liquid |
|---|---|---|---|---|
| Saline Absorbance | | | | |
| 1 | 50 | 13.6 | 36.4 | 72.8 |
| 2 | 50 | 6.8 | 43.2 | 86.4 |
| 4 | 50 | 4.7 | 45.3 | 90.6 |
| 8 | 50 | 1.9 | 48.1 | 96.2 |
| 16 | 50 | 0.5 | 49.5 | 99.0 |
| 32 | 50 | 0.0 | 50.0 | 100.0 |

EXAMPLE XIII

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 0.0 | 50.0 | 100.0 |
| Saline Absorbance | | | | |
| 1 | 50 | 11.7 | 38.3 | 76.6 |
| 2 | 50 | 8.5 | 41.5 | 83.0 |
| 4 | 50 | 4.4 | 45.6 | 91.2 |
| 8 | 50 | 3.6 | 46.4 | 92.8 |
| 16 | 50 | 0.6 | 49.4 | 98.8 |
| 32 | 50 | 0.0 | 50.0 | 100.0 |

EXAMPLE XIV

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 28.3 | 21.7 | 43.4 |
| 2 | 50 | 4.1 | 45.9 | 91.8 |
| 4 | 50 | 0.0 | 100.0 | 100.0 |
| Saline Absorbance | | | | |
| 1 | 50 | 34.3 | 15.7 | 31.4 |
| 2 | 50 | 17.0 | 33.0 | 66.0 |
| 4 | 50 | 7.6 | 42.4 | 84.8 |
| 8 | 50 | 6.3 | 43.7 | 87.4 |
| 16 | 50 | 4.5 | 45.5 | 91.0 |
| 32 | 50 | 1.6 | 48.4 | 96.8 |

EXAMPLE XV

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 13.6 | 37.4 | 74.8 |
| 2 | 50 | 0.0 | 50.0 | 100.0 |
| Saline Absorbance | | | | |
| 1 | 50 | 23.8 | 26.1 | 52.2 |
| 2 | 50 | 18.3 | 31.7 | 63.4 |
| 4 | 50 | 5.7 | 44.3 | 88.6 |
| 8 | 50 | 7.9 | 42.1 | 84.2 |

-continued

| Elapsed Time in Minutes | Starting Quantity of Liquid in Grams | Grams Retrieved Liquid | Grams Absorbed Liquid | Percent Absorbed Liquid |
|---|---|---|---|---|
| 16 | 50 | 4.5 | 45.5 | 91.0 |
| 32 | 50 | 4.8 | 45.2 | 90.4 |

EXAMPLE XVI

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 4.7 | 45.3 | 90.6 |
| 2 | 50 | 0.0 | 50.0 | 100.0 |
| Saline Absorbance | | | | |
| 1 | 50 | 18.8 | 31.2 | 62.4 |
| 2 | 50 | 9.9 | 40.1 | 80.2 |
| 4 | 50 | 6.9 | 43.1 | 86.2 |
| 8 | 50 | 3.9 | 48.4 | 92.2 |
| 16 | 50 | 1.6 | 48.4 | 96.8 |
| 32 | 50 | 2.4 | 47.6 | 95.2 |

EXAMPLE XVII

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 0.2 | 49.8 | 99.6 |
| 2 | 50 | 0.0 | 50.0 | 100.0 |
| Saline Absorbance | | | | |
| 1 | 50 | 15.5 | 34.5 | 69.0 |
| 2 | 50 | 9.2 | 40.8 | 81.6 |
| 4 | 50 | 4.8 | 45.2 | 90.4 |
| 8 | 50 | 4.8 | 45.2 | 90.4 |
| 16 | 50 | 2.2 | 47.8 | 95.6 |
| 32 | 50 | 1.0 | 49.0 | 98.0 |

EXAMPLE XVIII

| Elapsed Time in Minutes | Starting Quantity of Liquid in Grams | Grams Retrieved Liquid | Grams Absorbed Liquid | Percent Absorbed Liquid |
|---|---|---|---|---|
| $H_2O$ Absorbance | | | | |
| 1 | 50 | 0.2 | 49.8 | 99.6 |
| Saline Absorbance | | | | |
| 1 | 50 | 8.8 | 42.1 | 82.4 |
| 2 | 50 | 9.4 | 40.6 | 81.2 |
| 4 | 50 | 2.9 | 47.1 | 94.2 |
| 8 | 50 | 2.0 | 48.0 | 96.0 |
| 16 | 50 | 0.5 | 49.5 | 99.0 |
| 32 | 50 | 2.5 | 47.5 | 95.0 |

EXAMPLE XIX

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 7.9 | 42.1 | 84.2 |
| 2 | 50 | 0.0 | 50.0 | 100.0 |
| Saline Absorbance | | | | |
| 1 | 50 | 14.4 | 35.6 | 71.2 |
| 2 | 50 | 10.5 | 39.5 | 79.0 |
| 4 | 50 | 8.4 | 41.6 | 83.2 |
| 8 | 50 | 8.0 | 42.0 | 84.0 |
| 16 | 50 | 9.5 | 40.5 | 81.0 |
| 32 | 50 | 0.3 | 49.7 | 99.4 |

EXAMPLE XX

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 4.3 | 45.7 | 91.4 |
| 2 | 50 | 0.0 | 50.0 | 100.0 |
| Saline Absorbance | | | | |
| 1 | 50 | 14.3 | 35.7 | 71.4 |
| 2 | 50 | 10.9 | 39.1 | 78.2 |
| 4 | 50 | 3.0 | 47.0 | 94.0 |
| 8 | 50 | 1.7 | 48.3 | 96.6 |
| 16 | 50 | 0.0 | 50.0 | 100.0 |

EXAMPLE XXI

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 4.1 | 44.9 | 89.8 |
| 2 | 50 | 0.0 | 50.0 | 100.0 |
| Saline Absorbance | | | | |
| 1 | 50 | 14.2 | 35.8 | 71.6 |
| 2 | 50 | 10.5 | 39.5 | 79.0 |
| 4 | 50 | 6.7 | 43.3 | 86.6 |
| 8 | 50 | 2.4 | 47.6 | 95.2 |
| 16 | 50 | 1.2 | 48.8 | 97.6 |
| 32 | 50 | 0.0 | 50.0 | 100.0 |

EXAMPLE XXII

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 10.4 | 39.6 | 79.2 |
| 2 | 50 | 0.0 | 50.0 | 100.0 |
| Saline Absorbance | | | | |
| 1 | 50 | 13.8 | 36.2 | 72.4 |
| 2 | 50 | 10.8 | 39.2 | 78.4 |
| 4 | 50 | 3.0 | 47.0 | 94.0 |
| 8 | 50 | 0.2 | 49.8 | 99.6 |
| 16 | 50 | 0.0 | 50.0 | 100.0 |

EXAMPLE XXIII

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 19.4 | 30.6 | 61.2 |
| 2 | 50 | 6.1 | 33.9 | 67.8 |
| 4 | 50 | 9.6 | 40.4 | 80.8 |
| 8 | 50 | 7.4 | 42.6 | 85.2 |
| 16 | 50 | 2.1 | 47.9 | 95.8 |
| Saline Absorbance | | | | |
| 1 | 50 | 44.8 | 5.2 | 10.4 |
| 2 | 50 | 42.2 | 7.8 | 15.6 |
| 4 | 50 | 40.3 | 9.7 | 20.4 |
| 8 | 50 | 38.0 | 12.0 | 24.0 |
| 16 | 50 | 4.9 | 15.1 | 30.2 |
| 32 | 50 | 2.1 | 17.9 | 35.8 |

EXAMPLE XXIV

| Elapsed Time in Minutes | Starting Quantity of Liquid in Grams | Grams Retrieved Liquid | Grams Absorbed Liquid | Percent Absorbed Liquid |
|---|---|---|---|---|
| H₂O Absorbance | | | | |
| 1 | 50 | 25.3 | 24.7 | 49.4 |
| 2 | 50 | 21.4 | 28.6 | 57.2 |
| 4 | 50 | 19.1 | 30.9 | 61.8 |
| 8 | 50 | 11.7 | 38.3 | 76.6 |
| 16 | 50 | 11.4 | 38.6 | 77.2 |
| 32 | 50 | 1.5 | 48.5 | 97.0 |
| Saline Absorbance | | | | |
| 1 | 50 | 16.8 | 33.2 | 66.4 |
| 2 | 50 | 18.9 | 31.1 | 62.2 |
| 4 | 50 | 14.7 | 35.3 | 70.6 |
| 8 | 50 | 18.3 | 31.7 | 63.4 |
| 16 | 50 | 8.5 | 31.5 | 63.0 |
| 32 | 50 | 5.0 | 35.0 | 70.0 |

Example 24 represents a composition outside of the scope of the present invention. Where the sodium carboxymethylcellulose gum was examined as an absorber of water and saline. Example 23, which although representing the present invention is not a preferred embodiment for polysiloxane and wetting agent were eliminated. The composition of Example 23 exhibited a very low rate of wetting and did not form a solid gel at 1.5 parts to 50 parts water or saline while creating a "slimy" liquid which reached 95.8% absorbance in water in 16 minutes and only 35.8% absorbance in saline in 32 minutes. This should be compared to the product of Example 22 where at 1.5 parts to 50 parts water or saline the product formed a very solid gel in water and in two minutes exhibited 100% absorption and a very solid gel in saline in four minutes with 94% absorption and 100% absorption in 16 minutes.

As previously noted, Example 24 illustrates the use of a sodium carboxymethyl cellulose gum employed as an "absorber" Without further processing. Obviously, it proved most unsatisfactory as it never gelled to immobilize the liquid but instead formed a "slimy" thick liquid. It took 32 minutes to reach 97% absorbance in water and only 70% absorbance was observed at 32 minutes in saline.

It can further be noted from the experimental results recited previously that a satisfactory super absorber can be prepared with or without a disinfectant (Example 7) and with or without fragrances (Examples 5 and 6). Example 8 further demonstrates that isopropyl alcohol can be employed to improve absorbance together with the addition of a silicone oil (Antifoam A).

Examples 9-13 further demonstrate the value of a final polish with an alcohol/water mix to increase the saline and water absorbance quantity and rate. In this regard, water should be present in between 1% and 10% of the weight of the sodium carboxymethyl cellulose gum. When this was used, a 100% absorbance of water was observed in one to two minutes of addition and over 90% of the saline was observed to be absorbed in 4 to 8 minutes.

Examples 14-18 parallel the compositions of Examples 9-13 with the addition of the oily disinfectant orthobenzylchlorophenol. It was observed that the rate and quantity of absorbance did not suffer in including the disinfectant component.

To make a truly disposable product, it is contemplated that the above-referenced composition be embodied in a water soluble fiber to manufacture a sheet or covering for use as an absorbent. It is contemplated that polyvinylalcohol fibers are preferred as these fibers are water soluble at water temperatures of approximately 10° C. to 100° C. with approximately 50° C. to 90° C. being most preferable. Kuralon water soluble PVA fibers sold by Kuraray can be employed in the 0.5-5.0 denier range with 1-4 denier being desirable and 1.5-2.0 denier being most desirable. Sheets of such material can be formed via knitting, weaving or can be configured as "non-woven" products as in the formation of a sheet by the mechanical intertanglement of fibers or by the entanglement of fibers by jets of cool water. Such formation techniques are well known to those skilled in the textile arts.

Sheets of the above-described materials generally have a weight in the range of 10-200 g per square yard with 20-80 g per square yard being desirable and 25-50 g per square yard being most desirable.

EXAMPLE XXV

A composition was prepared by first combining the dry ingredients comprising 865.0 g A-250 and 7785.0 g 7H4CF, both of which are carboxymethyl cellulose gums sold by Aqualon with 378 g aluminum sulfate as the trivalent ion source. These ingredients were added to a ball mill jar and mixed for five minutes.

The wet ingredients were individually mixed by adding 324 g benzoic acid and 9084.0 g ethanol which were rolled for 15 minutes until the benzoic acid fully dissolved. To this liquid was added 1944.0 g FC171, 156.0 g LpH Se which is a disinfectant sold by Calgon-Vestal and 156.0 g of Vesphene II Se, also a disinfectant. These latter ingredients were also rolled for 15 minutes and added to the benzoic acid/ethanol solution and shaken well. The liquid ingredients were added to the dry components forming a pasty composition which was rolled for 10 minutes. The mixture was then spread on a horizontal surface as a thin sheet and dried overnight. The composition was then sieved and it was found that it was capable of absorbing in excess of 1200 cc of saline, lactated ringers and water within a two-minute timespan. These results are particularly surprising in light of the fact that both the carboxymethyl cellulose gums employed are ordinarily water soluble and are incapable of absorbing any significant quantities of aqueous liquid without substantial mechanical intervention. Even with such intervention, the cellulose gums create nothing more than a gelatin-like mass within a body of aqueous media and are thus considered unacceptable as absorbents absent the modification conducted pursuant to the present invention.

EXAMPLE XXVI

An absorbent composition was prepared by mixing 61.2 g of ethanol with 31.2 g of FC171. To this liquid was added 11,688.0 g of 50003C which is a polyacrylamide/polyacrylic acid copolymer sold by Mazer Chemical Co. These various ingredients were rolled for 15 minutes and put to one side. In a separate mixing vessel, 61.2 g of aluminum sulfate was added to 31.2 g Sipernat 22Hr, 31.2 g soda ash, 31.2 g TSP and 24.8 g Dowicide A. These latter ingredients were, themselves, roll mixed for 15 minutes and then added to the fraction containing the polyacrylamide/polyacrylic acid copolymer. The mixture was then spread on a horizontal surface as a thin sheet and dried overnight. The composition was then sieved and it was found that it was capable of absorbing in excess of 1200 cc of saline, lactated ringers and water within a two-minute timespan. In light of the fact that the polyacrylamide/polyacrylic copolymer is not soluble in water, there was no need to separately mix the dry and wet ingredients as was the case when dealing with anionic polymers such as the carboxymethyl cellulose gums of the previous examples. Unlike the various carboxymethyl cellulose gums of the previous examples, the polyacrylamide/polyacrylic copolymer employed here is substantially insoluble in aqueous media. As such, there is no particular reason to mix the dry components separately from wet components in this instance.

I claim:

1. A consumable product wherein a granular absorbent composition is placed upon or within a suitable support, said granular absorbent composition comprising a dry particulate polymeric material characterized as having surface anionic reactive sites, having ionic bridges between various ionic group polymer chains substantially within each polymer particle formed by ionic bonding between said surface anionic reactive sites and a multivalent metal ion, and having a hydrophobic coating on said particular polymeric material, and further comprising a wetting agent, wherein said polymeric material comprises a member selected from the group consisting of glucosidics, acrylics, acrylic acid copolymers and polyacrylamide/acrylic acid copolymers, and said surface anionic reactive sites comprise carboxylic groups.

2. The consumable product of claim 1 wherein said support comprises a member selected from the group consisting of diapers, feminine hygiene products, incontinent pads, surgical dressings and towels.

* * * * *